United States Patent [19]
Stefano et al.

[11] Patent Number: 5,506,222
[45] Date of Patent: Apr. 9, 1996

[54] METHOD AND COMPOSITION FOR TREATING INCREASED ANDROGENIC ACTIVITY

[75] Inventors: Francisco J. E. Stefano, Buenos Aires; Dario N. R. Carrara, Hurlingham, both of Argentina

[73] Assignee: Laboratorios Beta S.A., Buenos Aires, Argentina

[21] Appl. No.: 114,874

[22] Filed: Aug. 31, 1993

Related U.S. Application Data

[63] Continuation-in-part of Ser. No. 926,561, Aug. 6, 1992, abandoned, which is a continuation of Ser. No. 766,439, Sep. 25, 1991, abandoned.

[51] Int. Cl.$^6$ ..................................... A61K 31/58
[52] U.S. Cl. .................... 514/173; 514/859; 514/864; 514/947
[58] Field of Search ........................... 514/173, 859, 514/864, 947

[56] References Cited

U.S. PATENT DOCUMENTS

| | | | |
|---|---|---|---|
| 3,909,816 | 9/1975 | Teeters | 340/237 |
| 4,311,481 | 1/1982 | Nelson | 8/564 |
| 4,316,893 | 3/1982 | Rajadhyaksha | 424/180 |
| 4,537,776 | 8/1985 | Cooper et al. | 514/424 |
| 4,552,872 | 11/1985 | Cooper et al. | 514/175 |
| 4,559,331 | 12/1985 | Nickisch et al. | 514/173 |
| 4,727,088 | 2/1988 | Scott et al. | 514/725 |
| 5,053,227 | 10/1991 | Chiang et al. | 424/488 |

OTHER PUBLICATIONS

Shaw, J. C., *J. Am. Acad. Dermatol.* 24: 236–243, 1991.
Muhlemann, M. F. et al., *British J. Dermatology* 115:227–232, 1986.
Hughes, B. R. et al., *British J. Dermatology* 118: 687–691, 1988.
Messina, M. et al., *Current Therapeutic Research* 34: 319–324, 1983.
Califano, L. et al., *Clin. Ther.* 135:193–199, 1990.
Pizzino, D. et al., *Giornali Italino Dermatologia Venerologia 122: 599–604, 1987.*
Walton et al., *British J. Dermatology* 114: 261–264, 1986.
Cooper, *J. of Pharmaceutical Sciences* 74 (88), 1984.
Aungst, B. J., *Pharm Res.* 6: 244–247, 1989.
Sasaki, H. et al., *Int'l J. of Pharmaceutics* 60: 177–183, 1990.
Mirejovsky, D. et al., *J. of Pharmaceutical Sciences* 75: 1089–1093, 1986.
Chien, *Transdermal Controlled Systemic Medications*, Marcel Dekker, Inc., New York, pp. 69–75, 1987.

*Primary Examiner*—Shean C. Wu
*Attorney, Agent, or Firm*—Darby & Darby

[57] ABSTRACT

The present invention relates to spironolactone contain compositions for application to an area of human skin afflicted with acne, seborrheic condition or hirsutism. N,N-dialkyl lauramides are used as permeation enhancers.

12 Claims, No Drawings

METHOD AND COMPOSITION FOR TREATING INCREASED ANDROGENIC ACTIVITY

This application is a continuation-in-part of U.S. Ser. No. 07/926,561 filed Aug. 6, 1992 (now abandoned), which is a continuation of U.S. Ser. No. 07/766,439 filed Sep. 25, 1991 (now abandoned).

FIELD OF THE INVENTION

This invention relates to a method for the administration of a systemically active antiandrogen, namely spironolactone, through the skin. The invention reveals a pharmaceutical formulation with good cosmetic properties and low irritation potential, useful for the topical treatment of acne vulgaris, seborrheic dermatitis and hirsutism. A preparation that delivers spironolactone, at a rate that would ensure therapeutic concentrations, at the site of action (the sebaceous glands), but will not produce an important spillover to the general circulation (to avoid undesirable systemic effects), should contain defined amounts of chemicals that minimize the barrier characteristics of the uppermost layer of the epidermis. Said chemicals are: oleic acid, 1-methyl-2 pyrrolidone, 2,2-dimethyl octanoic acid and N,N dimethyl lauramide/propylene glycol monolaureate or combinations thereof. As utilized throughout the description, the term "spironolactone" refers to aldactone 3-(3-oxo-7αacetylthio 17βhydroxy-androst-4-en-17αyl) propionic acid lactone having the formula:

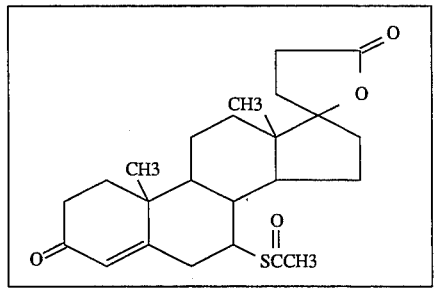

BACKGROUND OF THE INVENTION

The present invention relates to a method for the topical treatment of acne vulgaris, seborrhea and hirsutism with steroid spironolactone and, in particular, to a method that provides therapeutically useful concentrations of the antiandrogen at its site of action, the sebaceous gland, whilst maintains the spillover of the drug into the blood stream at a very low level, thus preventing systemic side effects.

Seborrheic acne is a dermatological disease with high prevalence in teenagers of both sexes. It is characterized by the presence of inflammatory lesions usually localized in cheeks and forehead. These lesions are often accompanied by comedones. When bacterial growth is prominent the lesions become suppurative. In the most severe cases, the lesions are spread over the back and chest. In these forms of acne there are formations of cysts with purulent accumulations that connect each other subcutaneously.

Due to its potential for leaving scars together with the profound effect that this has on teenager personality it is important to treat acne and seborrheic condition.

High doses of oral spironolactone have been successfully used in the treatment of acne as well as hirsutism Shaw, J. C., *J. Am. Acad. Dermat.* 24:236–243, 1991.

The bibliographical information related to the treatment of these affections by means of antiandrogens reveals that until now, said treatments has been confined to:

i) the administration of spironolactone "per os" that reaches to the hypodermis, the dermis and the most deep layers of epidermis to compete with or inhibit the tissular testosterone; and ii) topical applications of formulations containing spironolactone. The previously mentioned limited permeation of the epidermis external layer explains the reduced penetration of the spironolactone and the poor effects of said topical applications. The systemic use of spironolactone, however can cause a variety of side effects, endocrine (since it is an aldosterone antagonist), neurologic and gastrointestinal, with an incidence that ranges from 75 to 91% Muhlemann, M. F. et al, *British J. Dermatology* 115:227–232, 1986; Hughes, B. R. et al., *British J. Dermatology* 118:687–691, 1988.

To circumvent these effects topical spironolactone has been tried Messina, M. et al., *Current Therapeutic Research* 34:319–324, 1983; Califano, L. et al., *Clin Ther.* 135:193–199, 1990; Pizzino, D. et al., *Giornali Italiano Dermatologia Venerologia* 122:599–604, 1987. However, this administration route proved not to be successful in view of the scarcity of publications and lack of commercial success. Also Walton Walton et al., *British J. of Derm.* 114:261–264, 1986, proved that commercially available preparations did not reduce sebum excretion. The hypothesis can be raised that these failures are related to the fact that the formulations used did not provide suitable permeation of the applied steroid to the site of action and that most of the spironolactone remained in the outer surface of the skin without crossing the barrier imposed by the stratum corneum. It should be noted that the skin separates the internal organs from the outside environment and serves as a protective barrier against the penetration of chemicals. It is an organ composed of many histological layers, and is described in terms of 3 major multilaminate layers: the epidermis, the dermis and the hypodermis. The epidermis is composed of five strata: stratum germinativum, stratum spinosum, stratum granulosum, stratum lucidum and stratum corneum. The later consists of many layers of compacted, flattened, dehydrated and keratinized cells that are rather physiologically inactive and are continuously shed and replenished from the innermost layers. This layer, due to the physicochemical properties of its cells is the main resistance to the entrance of external agents and acts as an efficient barrier. Molecules moving from the environment into the skin must first penetrate the stratum corneum and migrate following a concentration gradient. To increase skin permeability and in particular the permeability of the stratum corneum, and the amount of drug delivery by topical application, the skin may be treated either with the application of one or more permeation enhancer agent or else the drug and the permeation enhancer may be applied together.

Another approach for increasing the amount of drug delivered into the skin might be to include a higher concentration of the pharmaceutically active drug in the pharmaceutical preparation. The increase in the concentration of the drug would hopefully augment the amount permeated. This concept might work up to a certain extent but is limited by the amount of drug which can be permeated through the skin barrier, that acts as a rate limiting step.

Various compounds for enhancing the permeability of skin are known in the art.

Perhaps the most famous of such penetration enhancers is DMSO (dimethyl sulfoxide). However DMSO has not received FDA approval. Another well known substance is Azone® (R), see U.S. Pat. Nos. 3,909,816 1-dodecyl-hexahydro-2H-azepin-2-ona (Nelson Research Development); 4,311,481 and 4,316,893. U.S. Pat. No. 4,537,776 Cooper, 1985, has an excellent summary of prior art in the use of binary systems for permeability increase of the stratum corneum.

Recently Cooper, in "Increased skin permeability for lipophilic molecules", published in *Journal of Pharmaceutical Sciences* Vol. 73 No. 88 (1984), disclosed the use of oleic acid as a penetration enhancer in the presence of propylene glycol (see also U.S. Pat. No. 4,537,776).

Neodecanoic acid has been shown to be a potent enhancer of naloxone permeation with a low irritation profile Aungst, B. J., *Pharm. Res.* 6:244–247, 1989. Also pyrrolidone derivatives have been shown to increase the permeability of the skin to several compounds by Sasaki, 1990, Sasaki, H. et al., *Int'l. J. of Pharmaceuticals* 60:177–183, 1990 and also lauramide derivatives by Mirejovsky and Takruri, 1986 Mirejovsky, D. et al., *J. of Pharm. Sci.* 75:1089–1093, 1986.

However, none of the above mentioned inventions or publications deals with the study of spironolactone.

Moreover as pointed by Chien in "Transdermal Controlled Systemic Medications", Marcel Dekker INC, New York 1987, pages 69–75, an enhancer increases the permeation of different compounds to different degree. There are not such general or universal enhancers. As an example we can quote results of this author as wherein below indicated:

| COMPOUND | AZONE | ENHANCEMENT FACTOR BY PROPYLOLEATE | PROPYL MYRISTATE |
|---|---|---|---|
| Progesterone | 6.0 | 5.4 | 4.6 |
| Estradiol | 20.2 | 14.6 | 9.3 |
| Hydrocortisone | 61.3 | 5.0 | 4.6 |
| Indomethacin | 14.5 | 4.7 | 3.8 |

This type of result clearly indicates that optimal permeation of a given compound can be achieved only by careful experimentation as shown in our Argentinean Patents Applications N. 315.433 and 314.479.

DETAILED DESCRIPTION

The present invention relates to a spironolactone containing composition for application to an area of human skin afflicted with acne, seborrheic condition or hirsutism for effective treatment thereof.

Applicants have discovered that the addition of N,N-dialkyllauramides, particularly the N,N-dimethyl lauramide, as skin permeation enhancers to said composition greatly increase the drug availability in relation to its site of action and that, at the same time, a residual action is obtained. The topical preparation herein described will have therapeutic effects but will avoid the undesirable side effects of the drug when administered orally.

The present invention proposes a treatment of testosterone-mediated skin disorders, administrating in a sustained and controlled manner, spironolactone directly to the dermal tissues where the testosterone is found. In this way, it is possible to have effective amounts of antiandrogens obtained in the required areas, thus avoiding the inconveniences of systemic route and the slowness of topical applications without employing the enhancer. The composition according to this invention comprises effective amounts, for example, 0.1 to 10% w/w, of spironolactone and N,N-($C_1$–$C_4$) dialkyllauramide as skin permeation enhancer for spironolactone, in a mixture of (1) emulsifying agents (2) solvent for spironolactone (3) buffer salts in amounts necessary to maintain a PH between 4.0 and 6.0 (4) water (5) preservative agents.

In order for a compound to be useful as a skin permeation enhancer the compound must meet a number of different requirements. Firstly, the compound must be a dermatologically acceptable compound which, when used topically on the skin, does not cause adverse side effects. Secondly, the compound must be compatible with spironolactone present in the pharmaceutical. Thirdly, the compound must have a substantial effect composition on increasing the permeability of spironolactone.

According to the present invention, the use of N,N-dimethyl lauramide as an enhancer has been studied as an enhancer of the residual effect of permeation of spironolactone. It has been studied. It has been observed that N,N-di ($C_1$–$C_4$) alkyl lauramide, and particularly, N,n-dimethyl lauramide warks as an enhancer of permeation with an effectivity higher than that of other enhancer compounds. Additionally, it has a residual effect on spironolactone, which has not been known so far. The N,N-dimethyl lauramide substantially differs from other known permeation enhancers in that noticeably increases the permeation of spironolactone as compared with other known permeation enhancers. In addition, it involves a residual action of the active drug, spironolactone, which is wholly novel regarding topical application of said drug. The term residual action refers to the persistence of the effect of the active drug, such as spironolactone, in almost equal intensity in spite of the removal of the active drug.

It has been researched and finally determined that the action of N,N-dimethyl lauramide with spironolactone can be further improved if used in combination with a specific additional enhancer.

The additional enhancer preferably is one of the known permeation enhancers described above and preferably as a fatty acid having 14, 10, 22 carbon atoms and one or more double bonds, a di ($C_1$–$C_4$) alkyl substituted fatty acid having 8 to 14 carbon atom, N-methyl pyrrolidone, or combinations of any of the foregoing. Most preferred additional enhancers are oleic acid, N-methyl pyrrolidone and neodecanoic acid.

Preferably, the amount of spironolactone will range from 0.1 to 10 percent w/w. Preferably, the amount of N,N-dimethyl lauramide will be in the range of 0.1 to 10% w/w. Preferably, the amount of additional enhancer will range from 0.1 to 10 percent w/w and most preferably from 2.5 to 10 percent w/w.

Also contemplated are pharmaceutical compositions comprising a safe, effective amount of spironolactone, preferably 0.1 to 10 percent w/w; a permeation enhancer comprising: N,N-di (lower or $C_1$–$C_4$ alkyl) lauramide and a pharmaceutically acceptable carrier; a pharmaceutical composition as above mentioned which can optionally comprise an additional enhancer. The pharmaceutically acceptable carrier includes one or more of buffers, preservatives, flavoring additives, and excipients in order to provide a cream having a cosmetic appearance.

The following formulation illustrates the composition of the present invention and is not to be construed as limiting the invention, either in spirit or in scope. It will be obvious to those skilled in the art that many modifications thereof may be made without departing from the purpose and intent of this disclosure.

The cream or ointment to which both, spironolactone and N,N-dimethyl lauramide, the skin permeation enhancer, are added for the purposes of this invention has the following general composition.

| Emulsifying wax | 8–20 | wt. percent |
|---|---|---|
| Liquid petrolatum | 2–10 | wt. percent |
| White petrolatum | 4–12 | wt. percent |
| Propyl Paraben | 0.05–0.1 | wt. percent |
| Methyl Paraben | 0.15–0.20 | wt. percent |
| Dehydrate sodium citrate | 0.6–1 | wt. percent |
| Citric acid, mohydrate | 0.2–0.7 | wt. percent |
| Purified water | 55–75 | wt. percent |
| Spironolactone | 05–10 | wt. percent |
| Permeation enhancer - N-N-dimethyl lauramide | 1–12 | wt. percent |

If necessary, up to 10% w/w of oleic acid or N-methyl pyrrolidone as additional enhancer, can be added to the formulation indicated in the above table.

Methods for Determining the Permeation Ratio of Spironolactone

Male mice, 8 to 16 weeks of age were shaved on their abdominal skin 72 hrs. before sacrifice by cervical dislocation. Only animals that showed absence of irritative lesions produced by the shaving were used. A section of full thickness abdominal skin was surgically excised and mounted between the two sections of a vertical diffusion cell having 2.2 cm$^2$ surface area, the epidermal layer facing up. A given amount of the pharmaceutical preparation containing different concentrations of spironolactone and a selected enhancer was spread over the epidermal layer whilst the dermal layer was in contact with a solution of ethanol/phosphate buffer, pH 7.4 40% v/v, at 34° C. The presence of spironolactone in the inferior cup (receptor phase) was monitored taking samples at given times and measured afterwards with an HPLC method.

EXAMPLE 1

A solution of 1 mg/ml or ≈0.1% spironolactone in propyleneglycol was put in the upper cell of the diffusion apparatus and the flux of spironolactone measured during the following 48 hrs. The flux was very low and not compatible with a therapeutic effect on the sebaceous glands. However, if oleic acid at a concentration of 10% is added to this solution there is a marked enhancement of the flux of spironolactone through the stratum corneum.

TABLE 1

PERMEATION OF SPIRONOLACTONE THROUGH MOUSE SKIN FROM A 1 mg/ml SOLUTION IN PROPYLENGLYCOL expressed as µg/cm$^2$

| TIME hrs | PROPYLENGLYCOL | PROPYLENGLYCOL + OLEIC ACID |
|---|---|---|
| 6 | 1.3 ± 0.2 | 87.0 ± 10.3 |
| 24 | 26.1 ± 16.8 | 523.0 ± 10.0 |
| 48 | 43.5 ± 14.3 | 1096.0 ± 200.0 |

This example shows that spironolactone has a very low permeability, that prevents the drug to reach its site of action, although this inconvenient can be overcome with the addition of an enhancer.

EXAMPLE 2

A cream containing 5% spironolactone was charged on top of the diffusion apparatus. The composition of thee cream was as follows: Spironolactone 5%, mixture of cet-earylalcohol and sodium laurylsulphate 9%, light mineral oil 6%, diisopropyl adipate 4.5%, white petrolatum 10.5%, mixture of glycerolmonoestearate and polyoxyethylene stearate 5%, propylparaben 0.05%, methylparaben 0.15%, citric acid monohydrate 0.5%, sodium citrate dehydrate 0.65% and water to 100%.

The cream thus prepared had excellent cosmetic appearance.

TABLE 2

PERMEATION OF SPIRONOLACTONE THROUGH MOUSE SKIN FROM A PHARMACEUTICAL COMPOSITION CONTAINING 5% SPIRONOLACTONE expressed as µg/cm$^2$

| TIME hrs | SPIRONOLACTONE PERMEATED |
|---|---|
| 3 | 5.6 ± 1.8 |
| 8 | 33.0 ± 5.5 |
| 24 | 354.0 ± 20.0 |

As shown in Table 2 spironolactone released from this pharmaceutical preparation crossed at a relative slow rate the skin.

EXAMPLE 3

In this example, the effect of adding either 2.5% or 5% or 10% isopropylmiristate to the pharmaceutical preparation above described was analyzed.

TABLE 3

SPIRONOLACTONE Permeation expressed as µg/cm$^2$

| TIME hrs | (n)) | NONE | (n) | 2.5% | (n) | 5% | (n) | 10% |
|---|---|---|---|---|---|---|---|---|
| 3 | 22 | 9.0 ± 1.6 | 5 | 13.2 ± 6.5 | 8 | 9.5 ± 176.0 | 10 | 17.3 ± 2.5 |
| 8 | 22 | 64.7 ± 7.5 | 5 | 59.6 ± 17.6 | 8 | 56.1 ± 10.4 | 10 | 90.3 ± 12.4 |
| 24 | 22 | 435.0 ± 23.0 | 5 | 419.0 ± 44.0 | 8 | 516.0 ± 98.0 | 10 | 811.0 ± 163.0 |

Values are MEAN±SEM, n indicated number of experiments. As shown in Table 3, only the highest concentration of isopropyl myristate produced an important increase in the flux of spironolactone across mouse skin.

EXAMPLE 4

In this example the effect of adding either 2.5% or 10% of propyleneglycol to the pharmaceutical preparation above described, was analyzed.

Propyleneglycol added to the pharmaceutical composition of Example No. 1 in the concentrations range between 2.5% and 10% did not produce an increased flux of spironolactone (see Table 4).

TABLE 4

| | | | | SPIRONOLACTONE Permeation expressed as $\mu g/cm^2$ | | | | |
|---|---|---|---|---|---|---|---|---|
| | | | | PROPYLENE GLYCOL CONTENT | | | | |
| TIME | (n)) | NONE | (n) | 2.5% | (n) | 5% | (n) | 10% |
| 3 | 22 | 9 ± 1.6 | 5 | 8.4 ± 0.5 | 6 | 4.5 ± 0.6 | 4 | 4.2 ± 0.6 |
| 8 | 22 | 64.7 ± 7.5 | 5 | 60.0 ± 11.0 | 6 | 26.5 ± 4.5 | 4 | 29.0 ± 4.7 |
| 24 | 22 | 434.8 ± 23.3 | 5 | 376.0 ± 47.0 | 6 | 422.0 ± 41.0 | 4 | 387.0 ± 93.0 |

EXAMPLE 5

The effects of several concentrations of oleic acid on spironolactone permeation were tested in conditions similar to those of the precedent example.

TABLE 5

| | | | | SPIRONOLACTONE Permeation expressed as $\mu g/cm^2$ | | | | |
|---|---|---|---|---|---|---|---|---|
| TIME | | | | OLEIC ACID CONCENTRATION | | | | |
| hrs | (n)) | NONE | (n) | 2.5% | (n) | 5% | (n) | 10% |
| 3 | 22 | 9 ± 1.6 | 5 | 8.7 ± 0.6 | 8 | 11.0 ± 1.0 | 9 | 22.0 ± 4.7 |
| 8 | 22 | 64.7 ± 7.5 | 5 | 67.0 ± 5.6 | 8 | 62.0 ± 8.4 | 9 | 123.0 ± 25.4 |
| 24 | 22 | 434.8 ± 23.3 | 5 | 523.0 ± 44.0 | 8 | 764.0 ± 99.0 | 9 | 1101.0 ± 151.8 |

In contrast to the results obtained with isopropyl myristate or propylene glycol, where either a slight increase or no increase in permeation was observed, oleic acid at 5% and 10% concentration produced a marked increase in permeation that was evident already at 3 hours.

compounds were less potent than oleic acid to increase permeation at early times although proved similar efficacy at 24 hrs.

TABLE 6

| | | | | SPIRONOLACTONE Permeation expressed as $\mu g/cm^2$ | | | | |
|---|---|---|---|---|---|---|---|---|
| TIME | | | | N-METHYL PYRROLIDONE CONCENTRATION | | | | |
| HRS | (n)) | NONE | (n) | 2.5% | (n) | 5% | (n) | 10% |
| 3 | 22 | 9.0 ± 1.6 | 5 | 11.4 ± 2.2 | 3 | 14.1 ± 1.5 | 4 | 7.7 ± 1.4 |
| 8 | 22 | 64.7 ± 7.5 | 5 | 56.5 ± 14.8 | 3 | 116.6 ± 12.2 | 4 | 56.9 ± 8.8 |
| 24 | 22 | 434.8 ± 23.3 | 5 | 443.9 ± 55.4 | 3 | 667.8 ± 70.4 | 4 | 993.8 ± 243.3 |

EXAMPLE 6

Following the procedure of the preceding examples, a series of tests utilizing either neodecanoic acid or N-methyl pyrrolidone were performed. The results showed that both

TABLE 6B

| | SPIRONOLACTONE Permeation expressed as µg/cm² | | | | | |
|---|---|---|---|---|---|---|
| TIME | | NEODECANOIC ACID CONCENTRATION | | | | |
| hrs | (n) | 2.5% | (n) | 5% | (n) | 10% |
| 3 | 5 | 10.9 ± 3.2 | 9 | 8.0 ± 0.9 | 9 | 10.2 ± 2.3 |
| 8 | 5 | 88.0 ± 27.0 | 9 | 70.5 ± 8.0 | 9 | 86.8 ± 21.0 |
| 24 | 5 | 879.0 ± 253.6 | 9 | 661.0 ± 83.0 | 9 | 925.7 ± 153.8 |

EXAMPLE 7

Once more, a similar test was performed using different concentrations of N,N-dimethyl lauramide. At the relative low concentration of 5% this compound showed a clear effect after 8 hrs. of incubation reaching a maximum effect with this concentration (TABLE 7).

TABLE 7

| | SPIRONOLACTONE Permeation expressed as µg/cm² | | | | | | | |
|---|---|---|---|---|---|---|---|---|
| TIME | | DIMETHYL LAURAMIDE CONCENTRATION | | | | | | |
| HRS | (n)) | NONE | (n) | 2.5% | (n) | 5% | (n) | 10% |
| 3 | 22 | 9 ± 1.6 | 5 | 10.0 ± 1.8 | 8 | 12.2 ± 2.8 | 10 | 17.4 ± 3.8 |
| 8 | 22 | 64.7 ± 7.5 | 5 | 75.4 ± 9.0 | 8 | 116.3 ± 21.5 | 10 | 88.8 ± 11.1 |
| 24 | 22 | 434.8 ± 23.3 | 5 | 777.2 ± 202.8 | 8 | 1037.4 ± 162.1 | 10 | 1195.7 ± 141.3 |

EXAMPLE 8

To test if prior application of the enhancer N,N-dimethyl lauramide will increase further the permeation of spironolactone the following experiments were performed. The abdominal skin of mice was shaved and during 72 hrs the area was covered 3 times per day with the pharmaceutical composition described in Example 3 (control group) or with this composition containing N,N-dimethyl lauramide. At the end of the period, the area was cleaned with water, excised and mounted in the cells. In these conditions, we measured the permeation of Spironolactone from either a cream containing 5% spironolactone or 5% spironolactone plus 10% N,N-dimethyl lauramide. As judged by the results reported in Table 10 the pretreatment greatly enhanced the permeation of spironolactone.

TABLE 8

| | SPIRONOLACTONE Permeation expressed as ratio |
|---|---|
| TIME hrs | PERMEATION RATIO PRETREATED DML/PRETREATMENT CONTROL |
| 3 | 6.5 ± 3.3 |
| 6 | 4.3 ± 1.8 |
| 24 | 4.1 ± 0.6 |

EXAMPLE 9

In this example the effect of different concentrations of propylene glycol monolaureate are demonstrated.

TABLE 9

| | SPIRONOLACTONE PERMEATION expressed as µg/cm² | | | |
|---|---|---|---|---|
| TIME | | PROPYLENGLYCOL MONOLAUREATE | | |
| hrs | NONE | 2.5% | 5% | 10% |
| 3 | 3 ± 0.07 | 8 ± 2.7 | 7 ± 1.7 | 17 ± 5 |
| 8 | 34 ± 3.6 | 60 ± 13 | 56 ± 22 | 118 ± 27 |
| 24 | 423 ± 29 | 487 ± 61 | 550 ± 113 | 933 ± 114 |

These results clearly show that this enhancer has a, potent effect in the early times. Thus the enhancing factor of 10% wall at 3 hours 5.6 and decreased to 2.2 at 24 hours. These results indicate a distinctive effect of this enhancer of great value for a topical cream.

Supplementary tests were made in order to compare the permeation ratio of spironolactone over that of the oleic acid (OA) and that of neodecanoic acid (NDA), two known enhancers used in the prior art, which have already been referred to above.

Table 10 refers to permeation measured on samples according to the present invention (DML 10% w/w) and the like with 10% oleic acid (OA) and 10% neodecanoic acid (NDA) under similar conditions. Skin was pre-treated with each enhancer, as described for Table 8.

The values in Table 10 show, apart from an absolute permeation (micrograms/cm²) of DML as compared with OA and NDA, a greater relative permeation (quotient of absolute permeation in Table 10 and control values), as shown in Table 11.

Further, the effects of pre-treatment on the enhancer as anticipated for Table 8, are then confirmed when comparing the absolute permeation found at 2194.4 micrograms/cm² for DML in Table 10 with permeation found for Table 7 at 1195.7 micrograms/cm² without pre-treatment.

TABLE 10

| SPIRONOLACTONE PERMEATION expressed as micrograms/cm² | | | | |
|---|---|---|---|---|
| SPIRONOLACTONE PERMEATION expressed as µg/cm² | | | | |
| TIME | | WITH PRETREATMENT | | |
| (h) | Control | DML 10% | OA 10% | NDA 10% |
| 3 | 12.8 ± 5.6 | 83.8 ± 40.2 | 17.0 ± 2.5 | 6.0 ± 1.8 |
| 8 | 95.4 ± 20.5 | 415.7 ± 163.1 | 142.2 ± 16.7 | 78.1 ± 26.0 |

TABLE 10-continued

| | SPIRONOLACTONE PERMEATION expressed as micrograms/cm$^2$ SPIRONOLACTONE PERMEATION expressed as µg/cm$^2$ | | | |
|---|---|---|---|---|
| TIME | | WITH PRETREATMENT | | |
| (h) | Control | DML 10% | OA 10% | NDA 10% |
| 24 | 534.3 ± 96.6 | 2194.4 ± 316.7 | 1353.1 ± 125.5 | 1092.3 ± 143.1 |

TABLE 11

| | SPIRONOLACTONE PERMEATION RATIO/CONTROL | | |
|---|---|---|---|
| | WITH PRETREATMENT | | |
| TIME (h) | DML 10%/ Control | OA 10%/ Control | NDA 10%/ Control |
| 3 | 6.52 | 1.33 | 0.47 |
| 8 | 4.36 | 1.49 | 0.82 |
| 24 | 4.11 | 2.53 | 2.04 |

While the above examples illustrate numerous embodiments of the invention, the scopes are limited only by the operability exhibited by improved permeation of spironolactone attributable to the incorporation of a chemical such as N,N-dimethyl lauramide to a common pharmaceutical preparation.

Also the results presented in these application clearly prove that at least for spironolactone there is no such an universal enhancer and that adequate fluxes across the skin can be achieved only by testing different types of compounds. Although prior art was useful for the theoretical approach, the results emerged from the careful investigation of multiple variables.

All patents, applications, articles, and test methods mentioned above are hereby incorporated by reference.

We claim:

1. A method to suppress the increased androgenic activity of the skin and to treat skin conditions related to hyper androgenic activity, said method comprising topically administering spironolactone together with a permeation enhancer, wherein said permeation enhancer comprises (a) a N,N-di($C_1$–$C_4$) alkyl lauramide.

2. A method as defined in claim 1, wherein said enhancer wherein one additional enhancer is included, which is selected from the group consisting of:
   i) fatty acids having 14 to 22 carbon atoms and one or more double bonds,
   ii) di ($C_1$–$C_4$) alkyl substituted fatty acids having 8 to 14 carbon atoms; and
   iii) N-methyl pyrrolidone.

3. A method as defined in claim 1, wherein said N,N-di($C_1$–$C_4$) alkyl lauramide is N,N-dimethyl lauramide.

4. A method as defined in claim 3, wherein said enhancer is selected from the group consisting of N,N-dimethyl lauramide/oleic acid, N,N-dimethyl lauramide/N-methyl pyrrolidone, and N,N-dimethyl lauramide/neodecanoic acid.

5. A method as defined in any of claim 1, 2, 3 or 4 wherein the amount of spironolactone ranges from 0.1 to 10 percent w/w.

6. A method as defined in any of claims 2, 3, or 4 wherein the N,N-di($C_1$–$C_4$)alkyl lauramides are present in a concentration of from 0.1 to 10 percent w/w.

7. A method as defined in claim 2 wherein the amount of said additional enhancer ranges from 0.1 to 10 percent w/w.

8. A pharmaceutical composition for the topical application or spironolactone to reduce the increased androgenic activity of the skin comprising:
   (a) a safe effective amount of spironolactone ranging from 0.1 to 10 percent w/w,
   (b) a permeation enhancer comprising N,N-di ($C_1$–$C_4$) lauramide; and
   (c) a pharmaceutically acceptable vehicle.

9. A pharmaceutical composition as defined in claim 8, which further comprises an additional permeation enhancer.

10. A pharmaceutical composition as defined in claim 8, wherein said vehicle includes buffers, preservatives, flavoring additives and excipients adapted to yield a cream having a cosmetic appearance.

11. A pharmaceutical composition as defined in claim 8 or 9 wherein said additional enhancer is selected from the group consisting of oleic acid, N-methyl-pyrrolidone and neodecanoic acid and wherein the amount of said additional enhancer ranges from 2.5 to 10 percent w/w.

12. A pharmaceutical composition as defined in claim 8 wherein said N,N-di($C_1$–$C_4$) lauramide is N,N-dimethyl-lauramide.

* * * * *